United States Patent [19]

Tadano et al.

[11] Patent Number: 5,719,036
[45] Date of Patent: Feb. 17, 1998

[54] QUANTITATIVE DETERMINATION METHOD FOR POTASSIUM IONS

[75] Inventors: Toshio Tadano, Shizuoka; Norihiko Kayahara, Kanagawa; Masao Umemoto, Saitama, all of Japan

[73] Assignee: Kyowa Medex Co., Ltd., Tokyo, Japan

[21] Appl. No.: 666,521

[22] PCT Filed: Jan. 20, 1995

[86] PCT No.: PCT/JP95/00052

§ 371 Date: Jul. 18, 1996

§ 102(e) Date: Jul. 18, 1996

[87] PCT Pub. No.: WO95/20052

PCT Pub. Date: Jul. 27, 1996

[30] Foreign Application Priority Data

Jan. 24, 1994 [JP] Japan .................................. 6-005955

[51] Int. Cl.$^6$ ................................................ C12Q 1/32
[52] U.S. Cl. ................................... 435/26; 435/962
[58] Field of Search ............................ 435/4, 18, 15, 435/25, 26, 69.2, 962

[56] References Cited

U.S. PATENT DOCUMENTS

| | | | |
|---|---|---|---|
| 5,334,507 | 8/1994 | Soya et al. | 435/25 |
| 5,380,649 | 1/1995 | Berry et al. | 435/22 |
| 5,384,246 | 1/1995 | Berry et al. | 435/22 |
| 5,384,247 | 1/1995 | Berry et al. | 435/22 |
| 5,409,814 | 4/1995 | Berry et al. | 435/22 |
| 5,501,958 | 3/1996 | Berry et al. | 435/18 |

*Primary Examiner*—Raph Gitomer
*Attorney, Agent, or Firm*—Fitzpatrick, Cella, Harper & Scinto

[57] ABSTRACT

The present invention relates to a method for quantitatively determining potassium ions in a sample using a glycerol dehydrogenase, which method is characterized by pretreating said sample with a glutamine synthetase in the presence of glutamic acid and adenosine triphosphate.

The method provides a clinical test which is capable of quantitatively determining potassium ions of an extremely low concentration even in a sample containing ammonium ions or hydroxylamine.

3 Claims, 1 Drawing Sheet

QUANTITATIVE DETERMINATION METHOD FOR POTASSIUM IONS

BACKGROUND

1. Field of the Invention

The present invention relates to a method for quantitatively determining potassium ions which is useful for clinical tests.

2. Description of the Background Art

Japanese Unexamined Patent Publication/PCT No. 1-503596 discloses that a glycerol dehydrogenase may be used in a quantitative determination method for potassium ions. However, when ammonium ions are present in a sample, they interfere with a glycerol dehydrogenase reaction and thus an accurate determination cannot be achieved.

As a method for eliminating ammonium ions in a sample, there is known a method Of pretreating a sample with a glutamate dehydrogenase [Clinical Chemical Analysis II (Nitrogen-Containing Components), 2nd edition, Tokyo Kagaku Dojin Co., Ltd. (1979)].

It is known that a glutamine synthetase produces glutamine in the presence of adenosine triphosphate (ATP) using glutamic acid and ammonium ions as substrates [Enzyme Handbook, B. Maruo et al. (eds.), Asakura Shoten Co., Ltd. (1982)]. However, it has never been reported that the glutamine synthetase is used for the elimination of ammonium ions in a sample.

NADH or NADPH used in the method of eliminating ammonium ions in a sample by pretreating the sample with a glutamate dehydrogenase give an influence upon a glycerol dehydrogenase reaction, and raise the background. These facts constitute obstacles to the determination of potassium ions in the sample. Therefore, this method can not be applied to a method for quantitatively determining potassium ions in a sample with a glycerol dehydrogenase.

SUMMARY OF THE INVENTION

It is the object of the present invention to provide a method for quantitatively determining potassium ions using a glycerol dehydrogenase. Even though ammonium ion or hydroxylamine is contained in a sample, the method can quantitatively determine potassium ions of an extremely low concentrations.

The method of the invention for quantitative determination of potassium ions is characterized in that a sample is pretreated with a glutamine synthetase in the presence of glutamic acid and ATP prior to a method for quantitatively determining potassium ions in a sample using a glycerol dehydrogenase. This is illustrated schematically below.

1. Pre-treatment
Ammonium ion scavenging

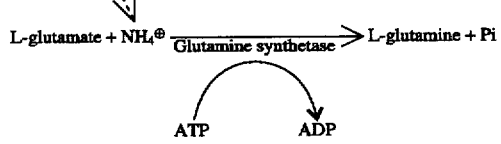

-continued
2. Potasssium Determination

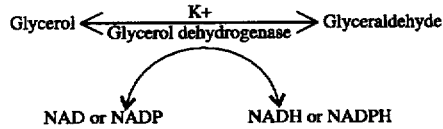

According to the invention, it is possible to quantitatively determine potassium ions of extremely low concentrations even in a sample containing ammonium ions or hydroxylamine.

In the present invention, any sample may be used; for example, body fluids such as blood and urine.

Now, preferred embodiments of the method of the invention for quantitative determination of potassium ions will be described below.

An aqueous medium is added to a sample, if necessary, then, 1–10 mM ATP, 1–10 mM glutamic acid, 2–50 mM magnesium and 1–100 KU/liter, preferably 1–50 KU/liter of a glutamine synthetase are added to the sample. The resultant solution is incubated at 20°–40° C. for 3–5 minutes to thereby carry out a pretreatment. Then, preferably in the presence of a chelating agent, 0.2–50 mM coenzyme, 0.05–2 KU/liter of a glycerol dehydrogenase and 2–500 mM substrate for the glycerol dehydrogenase are added and reacted at 8°–50° C. for 1–5 minutes. By measuring the activity of the glycerol dehydrogenase, it is possible to quantitatively determine the corresponding potassium ions. When at least one of the coenzyme used for the reaction, the glycerol dehydrogenase and the substrate for the glycerol dehydrogenase can be added after the pretreatment reaction, two other substance(s) can be added prior to the pretreatment reaction.

As an aqueous medium, any buffer may be used as long as it does not contain ammonium ions nor potassium ions. For example, glycine buffer, Tris buffer, Good's buffer, Veronal buffer, barbital buffer and 20 mM or below borate buffer may be enumerated. Preferably, these buffers have a concentration of 20–1000 mM and a pH value of 7–9.5.

The glutamine synthetase used in the invention may be any glutamine synthetase as long as it belong to the Enzyme No. 6.3.1.2. For example, natural enzymes derived from animal organisms, plant seeds, microorganisms, etc. or enzymes obtained by modifying such natural enzymes by genetic manipulation or the like may be enumerated.

As a chelating agent, any chelating agent may be used as long as it is capable of binding to a heavy metal such as copper, silver, zinc, mercury or iron. For example, ethylenediaminetetraacetic acid (EDTA), 2-hydroxyethylethylenediaminetriacetic acid (HEDTA), 1,2-diaminocyclohexanetetraacetic acid, nitrilotriacetic acid (NTA), diethylenetriaminepentaacetic acid (DTPA), glycoletherdiamine-N,N,N',N'-tetraacetic acid (GEDTA), ethylenediaminediacetic acid (EDDA), dihydroxyethylglycine (DHEG), ethylenediaminedipropionic acid hydrochloride (EDDP), 1,2-bis(o-aminophenoxy)ethane-N,N,N',N'-tetraacetic acid tetrapotassium salt (BAPTA) and hydroxyethyliminodiacetic acid (HIDA) may be enumerated. If a chelating agent is allowed to coexist in the reaction solution when a glutamine synthetase reaction takes place, it is particularly preferable to use GEDTA, EDDA, DHEG, EDDP, HIDA or BAPTA which is weak in the strength of bonding with magnesium. The addition of these chelating agents makes it possible to improve the linearity of a calibration curve in the determination method and, at the same time, to raise the upper limit of the concentration which can be determined by the method.

As a coenzyme, nicotinamide adenine dinucleotide (NAD) is used. When a reverse reaction of glycerol dehydrogenase is utilized, reduced NAD (NADH) is used as a coenzyme.

In the present invention, a glycerol dehydrogenase may be any enzyme as long as it is a glycerol dehydrogenase belonging to the Enzyme No. 1.1.1.6. However, enzymes derived from bacteria are preferable. Those enzymes which are obtained by modifying above enzymes by genetic manipulation, protein modification or the like may also be used. The commercial glycerol dehydrogenase used in the Examples is suitable for the determination method of the invention.

As a substrate for a glycerol dehydrogenase, usually, glycerol, 1,2-propanediol or 2,3-butanediol is used. However, when a reverse reaction of glycerol dehydrogenase is utilized, dihydroxyacetone (dimer) or the like is used as a substrate.

For measuring the glycerol dehydrogenase activity, any method may be used [Enzyme Handbook, B. Maruo et al. (eds.), Asakura Shoten Co., Ltd. (1982)]. In the case of a forward reaction, the enzyme activity is measured by quantitatively determining the change in the amount of NADH or NADPH generated. In the case of a reverse reaction, the enzyme activity is measured by quantitatively determining the change in the amount of NADH decreasing. When a reverse reaction is utilized, it is necessary to carry out a pretreatment to eliminate endogenous glycerol or to add a substrate excessively.

In the present invention, a surfactant such as polyethylene glycol alkylphenyl ether or a polyoxyethylene-polyoxypropylene condensation product, a solubilizer such as albumin, magnesium chloride or calcium chloride, and the like may be added to the aqueous medium.

DETAILED DESCRIPTION OF THE INVENTION

Figure 1:
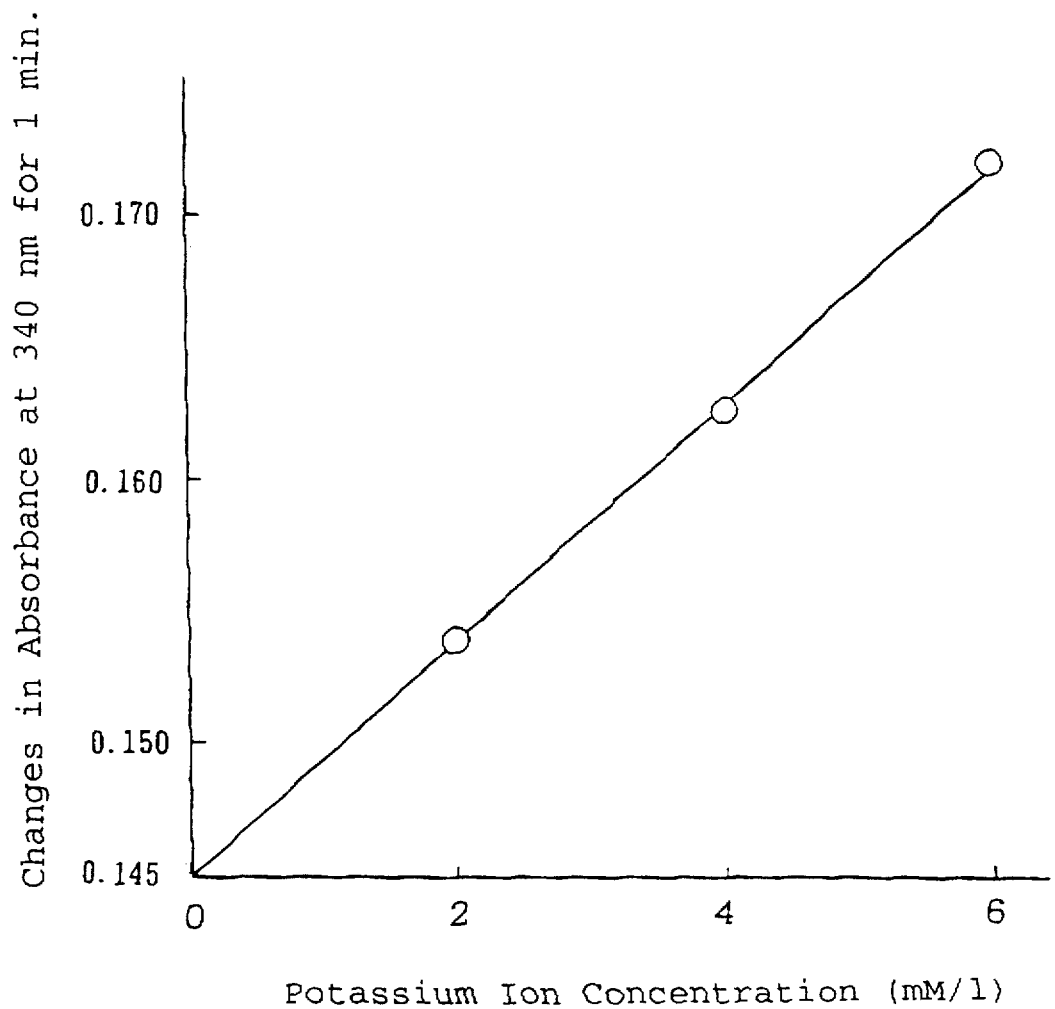
FIG. 1 is a graph showing a calibration curve for potassium ions obtained by the method of the invention.

The present invention will be described in more detail with reference to the following Examples, which should not be construed as limiting the scope of the present invention.

(Example 1)

Quantitative Determination in the Presence of Contaminants (1) Preparation of Standard Solutions for a Potassium Ion Calibration Curve Sodium chloride (Wako Pure Chemicals) and potassium chloride (Wako Pure Chemicals) were diluted with distilled water to thereby prepare standard solutions of 140 mM sodium ions as matrix with 2, 4 and 6 mM potassium ions, respectively, for obtaining a calibration curve for potassium ions.

(2) Quantitative Determination of Potassium Ions

In a test tube, 0.040 ml of the standard solution for a potassium ion calibration curve and 0.040 ml of 2 mM aqueous ammonium chloride (Wako Pure Chemicals) solution were placed (ammonium chloride was not added in the control test). To this sample solution, 2.0 ml of 300 mM Tris buffer (pH 8.5, 25° C.) containing 16 U/ml of glutamine synthetase (Unitika Ltd.), 1.2 mg/ml of L-glutamic acid (Wako Pure Chemicals), 0.5 mg/ml of magnesium chloride (Wako Pure Chemicals), 2 mg/ml of ATP (Oriental Yeast), 2 mg/ml of NAD (Oriental Yeast) and 12 mg/ml of glycerol (Boehringer Mannheim) were added and incubated at 37° C. for 5 minutes, to thereby eliminate ammonium ions.

Subsequently, 1 U/ml of glycerol dehydrogenase (Oriental Yeast) and 1 ml of 30 mM EDTA-containing 50 mM Tris buffer (pH 9.0, 25° C.) preincubated at 37° C. were added to the solution described above and agitated. Then, changes in absorbance at 340 nm were measured with a spectrophotometer (Hitachi Ltd.: UV3400). The calibration curve obtained is shown in FIG. 1.

The calibration curve shown in FIG. 1 was identical with the calibration curve obtained in the control test. This indicates that the amount of potassium ions can be determined accurately even in the presence of contaminants such as ammonia, if an appropriate method for eliminating the contaminants has been employed. In addition, the detection limit with the calibration curve obtained was not different from the detection limit in the determination method described in Reference Example 1 where a determination was conducted in the absence of ammonium chloride and without a pretreatment with a glutamine synthetase.

(Example 2)

Quantitative Determination of Potassium Ions in a Serum

A serum sample (0.040 ml) (which had been confirmed by flame photometry to contain 4.4 mM potassium ions) was placed in a test tube. To this sample, 2.0 ml of 250 mM Tris buffer (pH 9.0, 25° C.) containing 10 U/ml of glutamine synthetase (Unikita Ltd.), 5 mM/liter of L-glutamic acid (Wako Pure Chemicals), 5 mM/liter of magnesium sulfate (Wako Pure Chemicals), 5 mM/liter of ATP (Oriental Yeast), 2.5 mM/liter of NAD (Oriental Yeast) and 10 g/liter of glycerol (Boehringer Mannheim) were added and incubated at 37° C. for 5 minutes, to thereby eliminate ammonium ions.

Subsequently, 1 ml of 100 mM Tris buffer (pH 9.0, 25° C.) preincubated at 37° C. and containing 1.2 U/ml of glycerol dehydrogenase (Oriental Yeast) and 25 mM EDTA was added to the above solution and agitated. Then, changes in absorbance at 340 nm (between 4 minutes and 5 minutes from the beginning of the reaction) were measured with a spectrophotometer (Hitachi Ltd.: UV3400) and the amount of potassium ions were determined from the calibration curve. It was confirmed that 4.6 mM potassium ions were present in the serum.

(Reference Example 1)

Determination in the Absence of Contaminants and without a Pretreatment (1) Preparation of Standard Solutions for Obtaining a Potassium Ion Calibration Curve Potassium chloride (Wako Pure Chemicals) was diluted with distilled water to thereby prepare standard solutions for obtaining a calibration curve for 2, 4 and 6 mM potassium ions.

(2) Quantitative Determination of Potassium Ions

To a test tube, 0.040 ml of the standard solution for obtaining a potassium ion calibration curve was added and 300 mM Tris buffer (pH 8.5, 25° C.) containing 1.6 mg/ml of NAD (Oriental Yeast), 10 mg/ml of glycerol (Boehringer Mannheim) and 20 mM EDTA were added thereto. Then, 1 ml of an aqueous solution containing 1 U/ml of glycerol dehydrogenase (Oriental Yeast) was added to the above solution. After agitation of the resultant solution, changes in absorbance at 340 nm were measured with a spectrophotometer (Hitachi Ltd.: UV3400).

According to the present invention, there is provided a method for quantitatively determining potassium ions using a glycerol dehydrogenase, which method is capable of quantitatively determining potassium ions of an extremely low concentration even in a sample containing ammonium ions or hydroxylamine. The method of the invention for quantitative determination of potassium ions is useful for clinical tests.

We claim:

1. A method for quantitatively determining potassium ions a sample, comprising the steps of:

selecting a sample;

pretreating said sample with a glutamine synthetase in the presence of glutamic acid and adenosine triphosphate;

subjecting the pretreated sample to an enzyme reaction using a glycerol dehydrogenase; and correlating the result of said reaction with the quantity of potassium ions in the sample.

2. The method of claim 1, wherein the sample contains ammonium ions prior to said pretreatment.

3. The method of claim 1, wherein the sample is a body fluid.

* * * * *

UNITED STATES PATENT AND TRADEMARK OFFICE
CERTIFICATE OF CORRECTION

PATENT NO. : 5,719,036
DATED : February 17, 1998
INVENTOR(S) : TOSHIO TADANO, ET AL.

Page 1 of 2

It is certified that error appears in the above-indentified patent and that said Letters Patent is hereby corrected as shown below:

COLUMN 1

Line 11, "2." should read --2. Brief--; and
　　　Line 20, "Of" should read --of--.

COLUMN 2

Line 45, "belong" should read --belongs--.

COLUMN 3

Line 33, "a" should read --an--; and
　　　Line 34, "substrate excessively" should read
　　　　　　　--excess of substrate--.

COLUMN 4

Line 53, "were" should read --was--.

UNITED STATES PATENT AND TRADEMARK OFFICE
CERTIFICATE OF CORRECTION

PATENT NO. : 5,719,036
DATED : February 17, 1998
INVENTOR(S) : TOSHIO TADANO, ET AL.

It is certified that error appears in the above-identified patent and that said Letters Patent is hereby corrected as shown below:

<u>COLUMN 6</u>

Line 2, "ions" should read --ions in--;
  Line 10, "using" should read --with-- and "dehydrogenase;"
          should read --dehydrogenase; ¶ determining a result
          of said reaction--; and
  Line 14, "pretreatment" should read --pretreating--.

Signed and Sealed this

Twenty-second Day of September, 1998

Attest:

BRUCE LEHMAN

Attesting Officer         Commissioner of Patents and Trademarks